United States Patent [19]

Bradley et al.

[11] Patent Number: 5,050,607
[45] Date of Patent: Sep. 24, 1991

[54] HIGH RESOLUTION MAGNETIC RESONANCE IMAGING OF BODY CAVITIES

[75] Inventors: William G. Bradley, Pasadena; Lawrence W. Jones, San Marino, both of Calif.

[73] Assignee: Huntington Medical Research Institutes, Pasadena, Calif.

[21] Appl. No.: 403,918

[22] Filed: Sep. 1, 1989

Related U.S. Application Data

[63] Continuation of Ser. No. 21,758, Mar. 4, 1987, abandoned.

[51] Int. Cl.⁵ .............................................. A61B 5/055
[52] U.S. Cl. .......................... 128/653 A; 128/653 SC
[58] Field of Search ............... 324/307, 309, 318, 322; 128/653, 642, 786, 772; 604/21

[56] References Cited

U.S. PATENT DOCUMENTS

| | | | |
|---|---|---|---|
| 3,326,207 | 6/1967 | Egan | 128/642 |
| 4,304,239 | 12/1981 | Perlin | 128/642 |
| 4,572,198 | 2/1986 | Codrington | 128/653 |
| 4,672,972 | 6/1987 | Berke | 128/653 |

OTHER PUBLICATIONS

Boskamp, "Improved Surface Coil Imaging in Mr:Decoupling of the Excitation and Receiver Coils", *Radiology*, vol. 157, pp. 449–452, 1985.
Poon et al., "Magnetic Resonance Imaging of the Prostate", *Radiology*, 154, vol. 154, pp. 143–149, 1985.
Hrichk, "MR Imaging of the Prostate Gland: Normal Anatomy", *American Journal of Radiology*, vol. 148, pp. 51–58, Jan. 1987.
Doornbos, et al., "Application of Anatomically Shaped Surface Coils in MRI at 0.5T", *Magnetic Resonance in Medicine*, vol. 3, pp. 270–281, 1986.
Kantor et al., "A Catheter NMR Probe for in Vivo NMR Measurements of Internal Organs", The Society of the Magnetic Resonance in Medicine, Second Annual Meeting, Aug. 16–19, 1983, San Francisco, Calif., p. 192.

*Primary Examiner*—Ruth S. Smith
*Attorney, Agent, or Firm*—Christie, Parker & Hale

[57] ABSTRACT

A magnetic resonance (MR) imaging system includes a magnet for producing a magnetic field to which a patient is subjected, a radio frequency (RF) transmitter coupled to a body coil within the magnet, an RF receiver coupled to a surface coil within the magnet and placed as close as possible to tissue being analyzed by the MR imaging system, and a computer controlled system for generating RF signals sent from the transmitter and detected by the receiver for use in producing nuclear excitation and corresponding detected induced currents in the surface coil sent to an analog-to-digital converter and then to the computer for processing into an image display of the tissue under analysis. A preferred embodiment of the invention comprises surface coil apparatus for use in analyzing tissue within a body cavity of the patient, and a preferred system for use in analyzing the tissue of the prostate gland includes an elongated hollow tube for transrectal insertion, and expandable balloon sealed to the exterior of the tube, and a loop antenna surface coil wire secured to the exterior wall of the balloon. Fluid pressure applied to the inside of the tube and then to the interior of the balloon expands the balloon and thereby expands opposite sides of the surface coil wire and holds the surface coil antenna in a spaced apart expanded position useful in serving as a means for obtaining high resolution imaging of prostatic tissue.

29 Claims, 2 Drawing Sheets

HIGH RESOLUTION MAGNETIC RESONANCE IMAGING OF BODY CAVITIES

Cross-Reference to Related Applications

This is a continuation of application Ser. No. 07/021,758, filed 03/04/87 now abandoned.

FIELD OF THE INVENTION

This invention relates to magnetic resonance imaging, and more particularly, to use of an improved surface coil for providing high resolution magnetic resonance imaging of tissue in body cavities.

BACKGROUND OF THE INVENTION

In the background description to follow, the present invention is described in relation to magnetic resonance (MR) imaging techniques used in the examination and diagnosis of the prostate gland, although the invention also may have application to MR imaging of tissues in other body cavities.

Carcinoma of the prostate is the second most common malignancy in the male population, and it also has the second highest death rate. Diagnostic blood tests for prostatic carcinoma are imperfect and the disease is often well advanced by the time it is first diagnosed. The traditional methods of diagnosing carcinoma of the prostate are mainly digital rectal examination and estimation of serum acid phosphatase levels. The digital examination remains the most useful diagnostic technique inasmuch as acid phosphatase activity can be normal while the tumor is still confined to the gland.

Sonographic examination has been reported to have good diagnostic results in the detection of carcinoma. However, benign diseases such as benign prostatic hypertrophy and chronic prostatitis can yield similar sonographic appearances.

Magnetic resonance imaging has recently been shown to produce high quality images of the human body. Briefly, MR imaging makes use of magnetic fields and radio frequency waves to generate intensity-modulated images from specific sections of the body. MR imaging systems generally include a large magnet for generating a magnetic field. The patient being analyzed is exposed to the magnetic field of the magnet. Hydrogen nuclei (protons) in the magnetic field resonate when exposed to radio waves of a correct frequency. For imaging purposes, the strong uniform magnetic field of the magnet is selectively altered in one or more directions, preferably by small magnetic fields produced by three separate gradient coils associated with the magnet. Current passing through the gradient coils linearly alters the magnetic field of the magnet in directions controlled by the gradient coils. Signal transmission and reception are produced through use of a radio frequency (RF) transmitter coupled to a transmitting coil or antenna within the imaging unit and an RF receiver coupled to a receiving coil or antenna also located in the imaging unit. The receiving coil is positioned as close to the patient as possible for maximum imaging sensitivity. The patient is often surrounded by a body coil which serves both as a transmitting and receiving antenna. Alternatively, the body coil can be used as a transmitting antenna only, and a separate surface coil is used as a receiving antenna. The surface coil can usually be placed closer to the tissues under examination than a single body coil. An RF oscillator generates radio waves of different frequencies. By controlling the magnetic field in a known way through a switching system that controls the current in the gradient coils, and by generating radio waves of a select frequency, the exact location at which the patient's body is imaged can be controlled. When the frequency of the RF signal is set for the exact value of the magnetic field, resonance occurs. Radio waves of the same frequency are emitted from the portion of the patient being imaged, which induces small currents in the receiving coil. The induced currents are detected to produce an output signal dependent upon the number of protons involved in the resonance and tissue-specific parameters T-1 and T-2. The variation in proton density in different areas of the patient's body produces good contrast in an MR image and is therefore useful in differentiating among different tissues of the human body. The output signal from the RF receiver is processed by a computer system to produce an image display so that clinical diagnosis can be made by visual inspection of the displayed image. The quality of the image display is critical. It is desirable to obtain an image having high resolution so that clinical diagnosis can be as precise as possible. High resolution imaging is also critical in detecting tumor growth at its earlier stages where treatment of the disease is still possible.

Use of a body coil as both the transmitter and receiver antenna yields MR images of the body which can be useful in many clinical situations. However, use of anatomically shaped surface coils for signal detection yields images with higher signal-to-noise ratio in comparison to the usual body coil. As a result, the surface coils yield MR images with much higher sensitivity and therefore more detail in the critical anatomical areas. Such surface coils are used for RF detection only and excitation is produced by the standard body coil. These surface coils have been successful in the past in obtaining reasonably good MR images for exterior anatomical regions of the patient's body.

Use of a body coil (as both the transmitter and receiver coil) has not yielded high resolution images of the prostate gland. Higher resolution imaging of the prostate is desirable to obtain high detail images for detecting prostatic carcinoma or benign prostatic hypertrophy at their earlier stages. The prostate gland tissue has a capsule which forms an outer wall of the gland. Present MR imaging techniques detect prostatic carcinoma, but only after it is too far advanced, where the cancer has passed through the capsule and invaded surrounding tissues. To date, MR imaging techniques have not developed high resolution images that have been shown to detect early malignant tumors within the prostate gland routinely before they have passed through the outer capsule and invaded surrounding structures.

The present invention provides an improved MR imaging system that produces high resolution images of the prostate and tissues within other body cavities. With the present invention, detection of prostatic carcinoma and other malignant tumors at their earlier stages of growth is possible, when compared with use of a single body coil as both the transmitter and receiver in the MR imaging system.

SUMMARY OF THE INVENTION

Briefly, one embodiment of the invention comprises an improved surface coil apparatus for use in an MR imaging system which includes a magnet for producing a magnetic field to which a patient is subjected, an RF transmitter coupled to a body coil within the magnet, an RF receiver coupled to the surface coil, and means for generating RF signals sent from the transmitter and detected by the receiver for use in producing an MR image display of a portion of the patient's body. The improved surface coil apparatus obtains high resolution MR images of tissues within a body cavity of the patient. The apparatus includes a flexible electrically conductive element adapted for use as the surface coil antenna portion of the MR imaging system. The conductive element is movable between a normal position and an outwardly expanded position in which portions of the conductor are expanded apart from one another and held in their expanded spaced apart position so that the electrically conductive element can be effectively used as a surface coil for detection of RF signals in the MR imaging system. The surface coil apparatus is passed into the body cavity of the patient while the surface coil element is in its normal collapsed position, after which the coil is expanded and held in that position while the coil is operated as the receiver, antenna for the MR imaging system. Means are also provided for retracting the electrically conductive element back to its normal position for use in withdrawing the surface coil element from the body cavity once MR imaging of the tissues is completed.

In a preferred form of the invention, the surface coil is secured to the exterior of an inflatable balloon. Fluid such as air under pressure is applied to the interior of the balloon from a remote location so as to expand opposite sides of the surface coil apart to increase the area of the tissue being imaged by the MR system. The inflating fluid then can be removed from the balloon to retract the surface coil back to its normal position prior to its being withdrawn from the patient.

This system is useful in placing the surface coil as close as possible to the tissue under analysis in the body cavity. In one embodiment of the invention involving MR imaging of the prostate gland, the expandable surface coil is passed through the rectum to a position close to the prostate gland. The surface coil is then expanded so that opposite sides of the coil are held approximately parallel to a coronal plane through the gland at which imaging is directed. The inflating pressure outwardly on the opposite sides of the expanded surface coil can hold the coil in its fixed parallel position to obtain high resolution MR imaging of the entire transverse section of the prostate.

These and other aspects of the invention will be more fully understood by referring to the following detailed description and the accompanying drawings.

DETAILED DESCRIPTION

Figure 1:
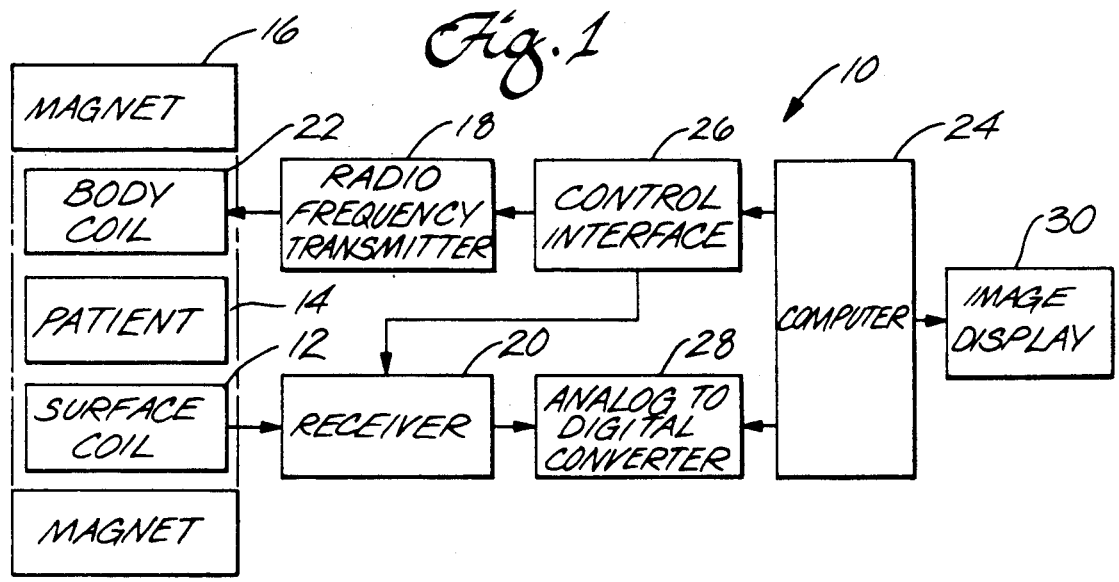
FIG. 1 is a schematic block diagram illustrating a typical MR imaging system with which the surface coil of this invention can be used.

FIG. 1 is a schematic block diagram illustrating basic components of an MR imaging system 10. The present invention includes an expandable surface coil apparatus 12 for use in diagnosing a patient 14 utilizing the MR imaging system. The block diagram of FIG. 1 is simply an example of a typical MR imaging system in which the surface coil apparatus can be used. In the description to follow, the surface coil apparatus 12 of the present invention will be described with reference to its use in an MR imaging system known in the art as a 0.35 Tesla (15 MHz) superconducting Diasonics MT/S Imaging System. However, the surface coil of this invention also can be adapted for use in other similar MR imaging systems by techniques known to those skilled in the art. Typical examples of MR imaging systems currently available to which the present invention can be adapted are those manufactured by General Electric, Philips, Picker, Siemens, CSG, El Scint, and Fonar, to name a few. The system also is described in the context of MR imaging of the prostate gland, but it will be apparent to those skilled in the art that the present invention also is adaptable for use in diagnosing tissues in other body cavities.

As illustrated in the block diagram of FIG. 1, the MR imaging system includes a large magnet 16 for establishing a magnetic field. A variety of magnets can be used. A superconducting magnet, resistive magnet or permanent magnet, common to most clinical MR imaging systems are examples. The patient being diagnosed is placed inside the magnet. The imaging system also includes gradient coils (not shown) for selectively altering the magnetic field in one or more directions. To accomplish this task preferably three separate gradient coils are used so that current flow through each of the gradient coils will linearly alter the magnetic field in directions controlled by the gradient coils. Signal transmission and reception for use in producing MR imaging are achieved through use of a radio frequency (RF) transmitter 18 and receiver 20. The patient is surrounded by a body coil 22 which is coupled to the RF transmitter and serves as a transmitting coil or antenna. When imaging the prostate gland, the body coil is positioned around the abdominal area of the patient. The RF receiver 20 is coupled to the surface coil 12 which serves as a receiving coil or antenna for signals generated by the RF system. The surface coil is located inside the magnet and is positioned as close to the patient as possible for maximum sensitivity. For MR imaging of the prostate gland, the surface coil is placed as close to the prostate as possible in a manner described in more detail below. A computer system 24 with a large memory, temporary (disk) and permanent (magnetic tape) storage capabilities, processor, and a high-quality multiformat imager acquire, process, store and display a large volume of data associated with the imaging process. The computer system includes the conventional control interface 26 for controlling the RF transmitter 18 and receiver 20. An RF oscillator generates radio waves of different frequencies. When the frequency is appropriate for the exact value of the magnetic field, resonance occurs. Radio waves of the same frequency are emitted from the patient, inducing small currents in the surface coil. The induced currents are detected and sent to and analog-to-digital converter 28 which then supplies digital signals to the computer system 24 for use in image display. The computer system processes the signals produced by the RF system to produce high resolution images on an image display 30.

Figure 2:
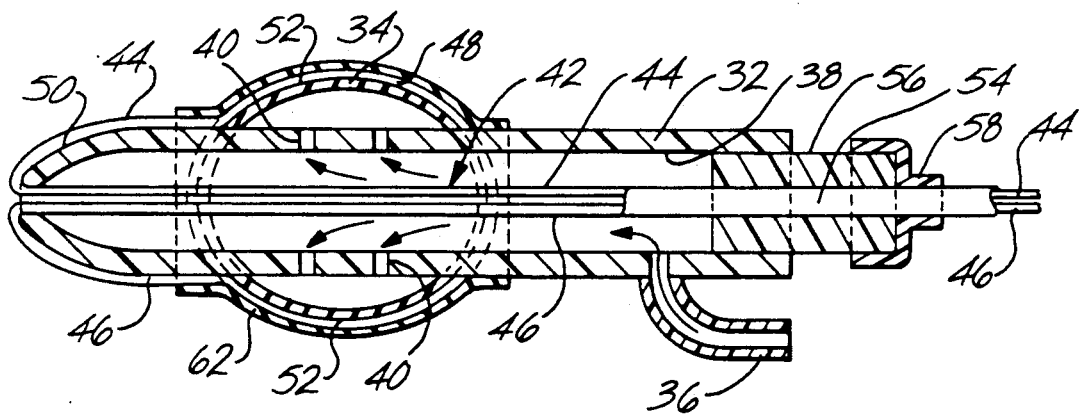
FIG. 2 is a fragmentary cross-sectional view of an expandable surface coil apparatus according to principles of this invention.

FIG. 2 illustrates details of the expandable surface coil apparatus 12, which includes a rigid elongated hollow tube 32 open at both ends. The tube can be a conventional barium enema tube. An inflatable balloon 34 is sealed at its ends around an exterior section of the tube so that the tube passes generally through the diameter of the balloon. The balloon is made from any suitable medical grade elastomer, and in one embodiment a Bardex balloon commonly used with a barium enema rectal catheter is used. The balloon is arranged relative to the outside diameter of the tube so that the balloon can be inflated to expand outwardly from the tube. In its normal collapsed position, the balloon wall loosely surrounds the outside diameter of the tube so that the collapsed state of the balloon generally matches the narrow profile of the tube outer wall. An air inlet 36 to the interior passage 38 of the tube can be connected to a supply (not shown) of air or other gas or inflating fluid under pressure for use in inflating the balloon. As illustrated by the arrows in FIG. 2, the inflating fluid flows from the interior passage 38 of the tube through ports 40 surrounding the tube to the interior of the surrounding balloon. The flexible wall of the balloon is expanded outwardly by the inflating pressure to progressively move outwardly away from the narrow profile tube to the inflated position of the balloon (illustrated in FIG. 2) in which the opposite walls of the balloon are spaced apart from the outside diameter of the tube. By retaining the inflating pressure within the balloon, the outer wall of the balloon can be held in its expanded position spaced apart from the outside diameter of the tube.

Figure 3:
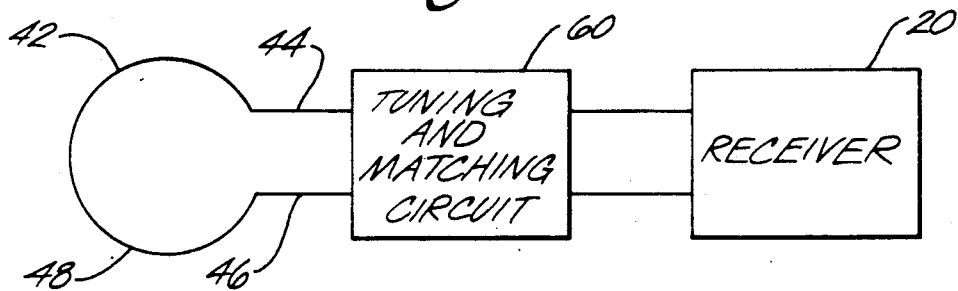
FIG. 3 is a schematic block diagram illustrating a tuning and matching circuit for producing RF signals in the MR imaging system.

The surface coil apparatus further includes a surface coil wire 42 in the form of a loop also illustrated schematically in FIG. 3. The surface coil wire preferably is an elongated flexible electrically conductive element in the form of a single continuous wire made from copper or other metal and electrically insulated in a conventional insulating jacket. In forming the surface coil wire as a loop, the surface coil can be defined as having opposite first and second lead portions 44 and 46, respectively, which extend closely parallel to one another before transitioning into an outer loop 48 expanded outwardly from the first and second lead portions of the coil. The coil is coupled to the tube 32 and balloon 34 by passing the long parallel first and second lead portions 44 and 46 of the coil through the long hollow interior of the tube. The opposite lead portions of the coil then emerge from the tip of the tube and pass over the outer wall of the tube at 50, near the tip of the tube. The loop portion 48 of the coil then passes around the exterior of the inflatable balloon 34 so that the conducting wire portions 52 of the loop are spaced apart from one another on opposite sides of the balloon. The portion of the loop farthest from the tip of the tube passes around one side of the tube adjacent the inner end of the balloon. Preferably, the portions 52 of the loop 48 in contact with the outer wall of the balloon are on a common diameter through the axes of the balloon (and through the central axis of the tube) so that the portions of the loop carried on the balloon are spaced approximately 180 degrees apart around the circumference of the balloon. The portions 52 of the loop carried on the balloon outer wall can be secured to the balloon by various means for achieving a rigid connection thereto; and in one embodiment, small sections of an adhesive tape (not shown) can be used to bond portions of the wire to the balloon. Moreover, the flexible opposite portions of the conductive wire are in a slack condition on the outside of the balloon when the balloon is in its normal or collapsed state to provide a sufficient axial dimension of the wire to accommodate outward flexing and expansion of the loop portion of the wire when the balloon is inflated. At the opposite end of the surface coil 42, the first and second lead portions 44 and 46 of the surface coil are preferably contained within a common electrically insulative outer jacket 54 which passes through end seals 56 and 58 for sealing off the fluid pressure inside the tube during inflation of the balloon. The lead portions 44 and 46 of the surface coil wire then pass to a tuning and matching circuit 60 illustrated schematically in FIG. 3. The expandable surface coil apparatus of FIG. 2 also includes an outer balloon 62 made of a suitable medical grade elastomer which can be removable for reuse of the surface coil apparatus on different patients.

The tuning and matching circuit 60 can be any of various circuit configurations for adapting an MR imaging system for use with a surface coil. As described above, the surface coil 42 is used for detection only. Excitation is achieved by use of the standard body coil 22. Tuning and matching of the surface coil and body coil are preferably controlled by electronic capacitors used in the circuit illustrated in FIG. 4. During excitation the receiver coil is detuned, and during signal detection the transmitter coil is damped. This successive detuning and damping is performed electronically via fast switching variable capacity diodes which are controlled by an applied voltage. The method of electronic tuning, matching and damping is described in further detail by Boskamp, *Radiology* 157:449–452 (1985), which is incorporated herein by this reference.

Figure 4:
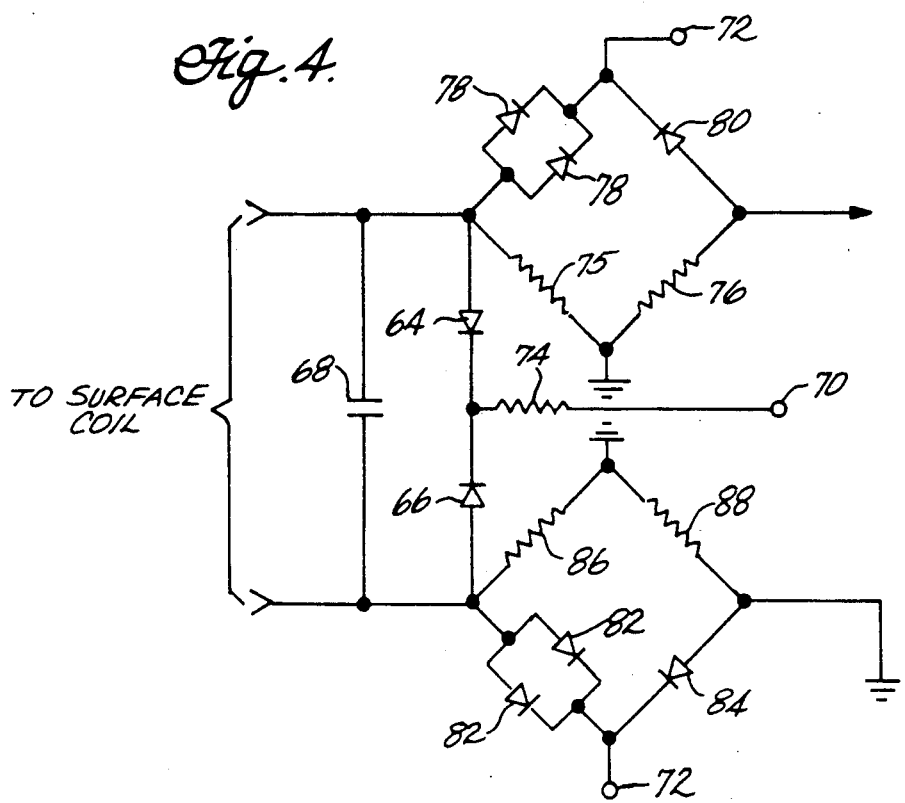
FIG. 4 is a schematic electrical diagram illustrating components of the tuning and matching circuit.

FIG. 4 illustrates a presently preferred tuning and matching circuit which includes reverse biased diodes 64 and 66 which are preferably variable capacitor diodes. These diodes are coupled to the surface coil input along with a variable capacitor 68. The variable capacitor diodes behave as a variable capacitor, the capacitance of which depends upon the reverse voltage across each diode. The variable capacitor diodes are used for fine-tuning the tuning and matching circuit in response to variable voltage signals at a tuning input 70 and matching outputs 72. The capacitor 68 is adjusted to the desired resonant frequency of the system. The matching outputs 72 are back-biased to the same voltage. These voltages are adjusted simultaneously. The tuning input is coupled to the receiver through the input resistor 74, the reverse biased diode 64, and a bridge circuit comprising resistors 75 and 76 having a common ground connection, and a diode pair 78 in series with a reverse biased diode 80. One matching output 72 is coupled to a second bridge circuit at a common connection between a diode pair 82 and a reverse biased diode 84. The second bridge circuit also includes a pair of resistors 86 and 88 with a common ground connection. The other matching output 72 is coupled to the first bridge circuit at a common connection between the diode pair 78 and the reverse biased diode 80. Resistors in the circuit shown in FIG. 4 are used to isolate the RF circuit from its environment. During an excitation pulse the impedance of the surface coil circuit is increased by switching the reverse voltage on the reverse biased diodes so as to increase the resonant frequency of the circuit. This induces a current in the surface coil coupled to the circuit. Tuning and matching are therefore achieved by DC voltage signals under computer control and induced currents in the surface coil are sent to the receiver and then to the analog-to-digital converter 28.

Inasmuch as two coils operating at the same resonant frequency are used, a coupling problem can develop. This problem can be solved by minimizing the mutual inductance or maximizing the impedance of the surface coil or resonant circuit during excitation, using a decoupling circuit described in the Boskamp article referred to above.

Figure 5:
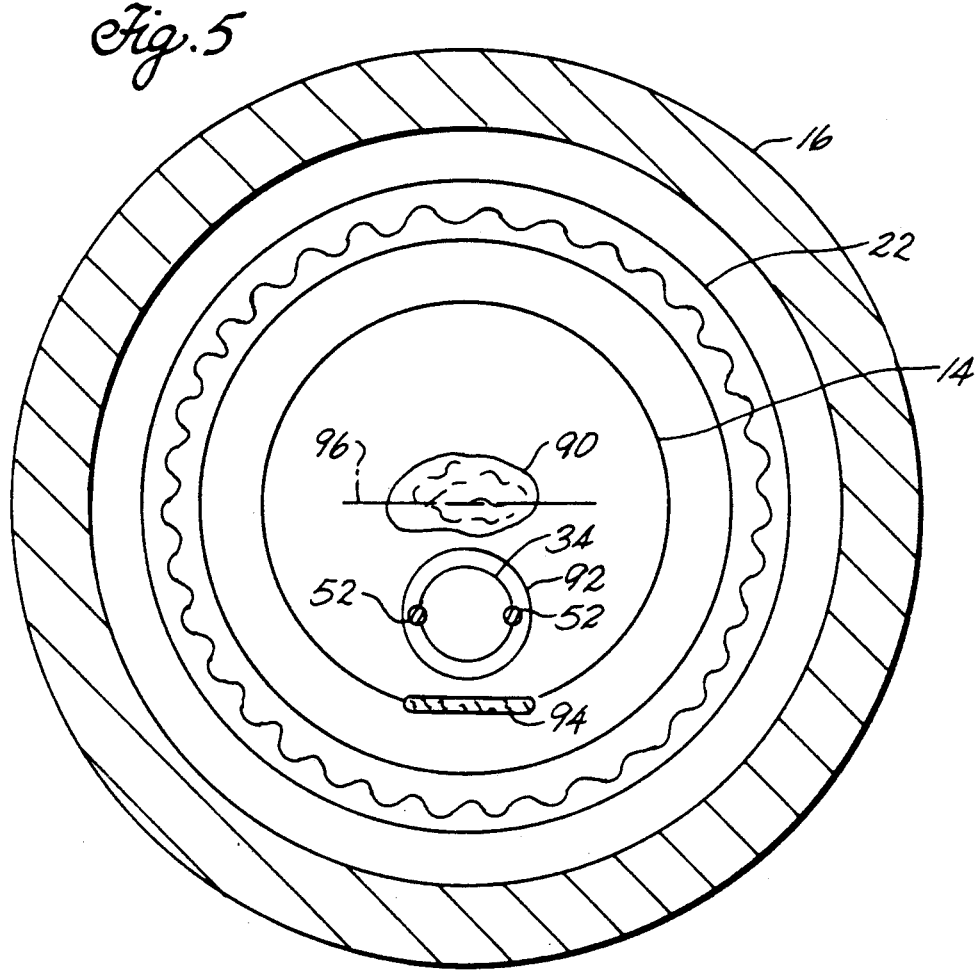
FIG. 5 is a schematic cross-sectional view illustrating use of the surface coil for MR imaging of the prostate gland.

In using the surface coil, the tube 32 is inserted transrectally with the balloon 34 in its normal or collapsed condition. This step is best illustrated in FIG. 5 which schematically illustrates the patient 14 with the surrounding body coil 22 inside the outer magnet 16. For orientation purposes, FIG. 5 also illustrates the prostate 90, rectum 92 and coccyx 94. The surface coil is inserted so that the coil is placed posterior to the prostate, as close to the gland as possible. The tube is orientated so that the opposite portions 52 of the loop formed by the surface coil are essentially parallel to the coronal imaging plane in the prostate, represented by the coronal axis 96 through the prostate gland, as illustrated in FIG. 5. Fluid pressure such as air is then applied to the interior of the tube to expand the balloon 34 outwardly so as to distend the loop portion of the surface coil wire to enlarge its diameter to approximately 5 cm. The balloon is held in its expanded condition for holding the opposite sides of the surface coil wire in their fixed expanded orientation during excitation by the body coil and detection of RF energy by the surface coil. In one experimental use, the balloon was positioned posterior to the prostate and images were acquired on a 256×256 matrix with 0.95 mm pixels. High resolution images of the prostate were obtained giving good depiction of the prostatic zonal anatomy. Images were substantially higher in resolution than corresponding images obtained with an MR imaging system using a body coil only for excitation and detection.

Test results indicated that lesions 3 to 4 mm. in size could be detected with the expandable surface coil of this invention, whereas the same lesions did not appear on images produced from the same patient by the use of an exterior body coil only. Images developed by experimental use of the invention have detected abnormal tissue with high resolution. It is expected that, with continued research and pathological data, clinical stages A or B of prostatic carcinoma may be detected. MR imaging using an exterior body coil only does not provide the resolution necessary to precisely detect stages A and B and has thus far only been able to detect extracapsular malignant growth after it has invaded surrounding tissues.

Use of the surface coil of this invention also has shown that best results are obtained when the expanded coil wires of the surface coil are approximately parallel to the coronal imaging plane through the prostate. This ensures uniformity of the image. Moreover, by expansion of the surface coil wire portions 52 to a sufficiently large spacing relative to the width of the prostate, the surface coil ensures a complete image of the prostate tissue. Any twisting of the coil about the axis of the tube to a position in which opposite sides of the loop are offset at an angle to the coronal axis 96 through the prostate can produce high signal rear-field artifact with image degradation (where the antenna coil is too close to the gland) or produce image portions having poor resolution (where the coil is positioned too far from the prostate).

Although the invention has been described in relation to its use in MR imaging of the prostate gland, tissues in other body cavities, including oral, vaginal, gastrointestinal and rectal uses of the expandable surface coil are possible, without departing from the scope of the invention.

Moreover, although use of the surface coil in its expanded condition has been illustrated in the context of an inflatable balloon for expanding the surface coil loop outwardly once the coil is in place inside the body cavity, other techniques for expansion and retraction of the flexible surface coil also are possible without departing from the scope of the invention. For instance, a spring-loaded electrically insulated surface coil can be used. The coil can be inserted into the body cavity in a collapsed or retracted position, after which the spring can be activated remotely to expand opposite sides of the coil outwardly to a spaced apart distance sufficient for imaging the desired area of the tissue under analysis. The spring-loaded pressure remains applied on the coil, preferably by outward pressure constantly applied from within the loop formed by the coil. The spring force then can be released to retract the coil.

We claim:

1. An MR imaging system which includes:
a magnet for producing a magnetic field to which a patient is subjected,
an RF transmitter coupled to a body coil within the magnet,
an RF receiver wherein RF signals generated by the RF transmitter are sent from the RF transmitter and detected by the RF receiver,
a surface coil apparatus for use in producing high resolution MR images of tissue within a body cavity of the patient, the surface coil apparatus comprising:
   (a) support means adapted for insertion into and withdrawal from said body cavity;
   (b) a flexible antenna wire mounted on the support means and having a normal position in which portions of the antenna wire are spaced apart from one another;
   (c) means mounted on the support means for expanding said portions of the antenna wire apart from one another to an expanded position wherein said portions of the antenna wire are held in their expanded spaced apart relation so that the expanded position of the antenna wire can be used for detection of RF signals generated by said transmitter to produce an image of body tissues located adjacent the antenna wire; and
   (d) means for contracting said portions of the antenna wire to the normal position for use in withdrawing the supporting means and the antenna wire thereon from the body cavity;
the RF receiver being coupled to the antenna wire for detecting RF signals induced in the antenna wire; and
processing means coupled to the RF receiver for converting the detected signals induced in the antenna wire into an MR image display of the body tissues located adjacent the antenna wire of the surface coil apparatus.

2. Apparatus according to claim 1 in which the means for expanding the antenna wire comprises a fluid inflatable balloon positioned inside the antenna wire.

3. Apparatus according to claim 2 including means for applying fluid pressure to the inside of the balloon from a remote location.

4. Apparatus according to claim 3 in which the means for contracting the antenna wire comprise means for depressurizing inside the balloon to collapse the balloon.

5. Apparatus according to claim 2 in which the support means includes an elongated tube, and including means for sealing the balloon to the wall of the tube so the tube extends through the hollow interior of the balloon; and in which the means for expanding the balloon includes means for passing fluid under pressure into the tube and from the tube to the interior of the balloon for expanding the balloon.

6. Apparatus according to claim 5 in which the antenna wire comprises a loop antenna in which opposite portions of the loop extend through the tube and pass out an end of the tube and then around opposite sides of the outer wall of the balloon so that fluid under pressure passing into the balloon expands the opposite portions of the loop antenna apart from one another.

7. Apparatus according to claim 6 including a tuning and matching circuit, the output of which is coupled to the RF receiver, and in which conductive ends of the loop antenna are coupled to the tuning and matching circuit.

8. Apparatus according to claim 1 in which the MR imaging system includes a tuning and matching circuit, and in which the body coil and antenna wire are tuned and matched by the tuning and matching circuit.

9. Apparatus according to claim 1 in which said portions of the antenna wire extend separately and axially along opposite sides of the support means.

10. An MR imaging system which includes:
a magnet for producing a magnetic field to which a patient is subjected,
an RF transmitter coupled to a body coil within the magnet,
an RF receiver coupled to a surface coil apparatus within the magnet, the surface coil apparatus providing means for obtaining high resolution MR images of tissue within a body cavity of the patient, and wherein RF signals generated by the RF transmitter are sent from the RF transmitter and detected by the RF receiver, the surface coil apparatus comprising:
 (a) an elongated narrow profile hollow tube adapted for insertion into and withdrawal from the body cavity;
 (b) an expandable balloon sealed to the exterior of the tube, the balloon having a normal relaxed position generally matching the normal profile of the tube and an expanded position spaced apart from the outer wall of the tube;
 (c) an antenna wire secured to the wall of the balloon so that portions of the antenna wire extend at least on opposite sides of the balloon wall; and
 (d) means for applying fluid pressure to the inside of the tube and then to the interior of the balloon to expand the balloon and thereby expand said opposite portions of the antenna wire apart from one another to an expanded position useful for serving as a detection coil for detecting the RF signals generated by said RF transmitter for use in producing high resolution imaging of adjacent tissue within said body cavity;
the receiver being coupled to the antenna wire for detecting the RF signals induced in the antenna wire; and
processing means coupled to the RF receiver for converting the detected signals induced in the antenna wire into an MR image display of the tissue located within said body cavity adjacent the antenna wire.

11. Apparatus according to claim 10 in which the opposite portions of the antenna wire are secured to diametrically opposed exterior wall portions of the balloon.

12. Apparatus according to claim 11 in which the antenna wire is in the configuration of a loop antenna.

13. Apparatus according to claim 10 in which the antenna wire comprises a loop antenna in which opposite portions of the loop extend through the tube and pass out an end of the tube and then around opposite sides of the outer wall of the balloon so that fluid under pressure passing into the balloon expands the opposite portions of the loop antenna apart from one another.

14. Apparatus according to claim 13 in which conductive ends of the loop antenna are coupled to a tuning and matching circuit of the MR imaging system.

15. Apparatus according to claim 10 in which the MR imaging system includes a tuning and matching circuit, and in which the body coil and antenna wire are tuned and matched by the tuning and matching circuit.

16. Apparatus according to claim 10 in which said opposite portions of the antenna wire extend separately and axially along opposite sides of the balloon wall.

17. A method for obtaining high resolution MR imaging of the tissue within a body cavity of a patient in an MR imaging system which includes a magnet for producing a magnetic field to which the patient is subjected, an RF transmitter coupled to a body coil within the magnet, an RF receiver coupled to a surface coil within the magnet, and means for generating RF signals sent from the transmitter and detected by the receiver for use in producing an MR image display of a portion of the tissue within the body cavity of the patient, the method comprising:
positioning a surface coil apparatus in the body cavity, wherein said apparatus includes a flexible surface coil wire having a normal low-profile position and an expanded position, the surface coil apparatus being positioned with the surface coil wire in said normal position, and
thereafter expanding the surface coil wire to its expanded position, wherein said expanded surface coil wire is useful in producing high resolution imaging of the tissue in or adjacent to the body cavity when serving as said surface coil for detection of RF signals in said MR imaging system.

18. The method according to claim 17 in which the surface coil wire comprises an MR surface coil antenna loop having diametrically opposite sides expanded outwardly and retained in that position by outward pressure applied from within the loop.

19. A method according to claim 18 in which the diametrically opposed sides of the loop antenna are held spaced apart by a distance equal to at least about the maximum width of the body tissue under diagnosis.

20. A method according to claim 18 in which the diametrically opposed sides of the loop antenna are retained in their expanded position via an expandable balloon to which the loop antenna is secured.

21. The method according to claim 20 in which the expandable balloon is inflated to the expanded position remotely by fluid pressure, which can be removed to return the balloon to its normal position for use in withdrawing the surface coil apparatus from the body cavity of the patient.

22. The method according to claim 17 including the step of maintaining the surface coil wire expanded in a plane approximately parallel to the coronal imaging plane of the prostate gland.

23. A method for obtaining high resolution MR imaging of the prostate gland in an MR imaging system which includes a magnet for producing a magnetic field to which a patient is subjected, an RF transmitter coupled to a body coil within the magnet, an RF receiver coupled to a surface coil within the magnet, and means for generating RF signals sent from the transmitter and detected by the receiver for use in producing an MR image display of a portion of the patient's prostate gland, the method comprising:

inserting a surface coil apparatus transrectally to a position adjacent the patient's prostate gland wherein said apparatus includes a flexible surface coil wire having a normal low profile position and an expanded position, the surface coil apparatus being positioned with the surface coil wire in said normal position, and thereafter expanding the surface coil wire to its expanded position wherein said expanded surface coil wire is useful in producing high resolution imaging of the tissue in the prostate gland when serving as said surface coil for detection of RF signals in said MR imaging system.

24. The method according to claim 23 in which the surface coil wire comprises an MR surface coil antenna loop having diametrically opposite sides, and including the step of expanding the opposite sides of the antenna loop outwardly and retaining them in that position by outward pressure applied from within the loop.

25. The method according to claim 24 including the step of maintaining the diametrically opposed sides of the loop antenna spaced apart by a distance equal to at least about the maximum width of the prostate gland.

26. The method according to claim 24 including the step of maintaining the diametrically opposed sides of the loop antenna in their expanded position via an expandable balloon to which the loop antenna is secured.

27. The method according to claim 26 including the step of inflating the expandable balloon to the expanded position remotely by fluid pressure.

28. The method according to claim 27 including removing the fluid pressure from the balloon to return the balloon to its normal position for use in withdrawing the surface coil apparatus from the patient.

29. The method according to claim 23 including the step of maintaining the surface coil wire expanded in a plane approximately parallel to the coronal imaging plane of the prostate gland.

* * * * *